United States Patent
Lauffer (10) Patent No.: US 8,396,735 B2
(45) Date of Patent: *Mar. 12, 2013

(54) METHOD AND SYSTEM TO CONNECT CONSUMERS TO INFORMATION

(75) Inventor: Randall B. Lauffer, Brookline, MA (US)

(73) Assignee: UTBK, LLC, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/768,664

(22) Filed: Apr. 27, 2010

(65) Prior Publication Data

US 2010/0208028 A1  Aug. 19, 2010

Related U.S. Application Data (63) Continuation of application No. 11/772,525, filed on Jul. 2, 2007, now Pat. No. 7,729,938, which is a continuation of application No. 10/951,502, filed on Sep. 27, 2004, now Pat. No. 7,249,045, which is a continuation of application No. 10/107,743, filed on (Continued)

(51) Int. Cl.
*G06Q 10/00* (2012.01)
(52) U.S. Cl. .................. 705/7.14; 379/265.12
(58) Field of Classification Search .......... 705/7.14; 379/265.12
See application file for complete search history.

(56) References Cited

U.S. PATENT DOCUMENTS

| | | |
|---|---|---|
| 4,751,669 A | 6/1988 | Sturgis et al. |
| 4,850,007 A | 7/1989 | Marino et al. |
| 4,963,995 A | 10/1990 | Lang |
| 5,057,932 A | 10/1991 | Lang |
| 5,058,152 A | 10/1991 | Solomon et al. |
| 5,148,474 A | 9/1992 | Haralambopoulos et al. |
| 5,164,839 A | 11/1992 | Lang |
| 5,262,875 A | 11/1993 | Mincer et al. |
| 5,325,424 A | 6/1994 | Grube |
| 5,347,632 A | 9/1994 | Filepp et al. |
| 5,359,508 A | 10/1994 | Rossides |
| 5,440,334 A | 8/1995 | Walters et al. |
| 5,524,146 A | 6/1996 | Morrisey et al. |
| 5,533,103 A * | 7/1996 | Peavey et al. .................. 379/69 |
| 5,539,735 A | 7/1996 | Moskowitz |
| 5,555,298 A | 9/1996 | Jonsson |

(Continued)

FOREIGN PATENT DOCUMENTS

| | | |
|---|---|---|
| AU | 699785 | 5/1995 |
| GB | 2329046 | 3/1999 |

(Continued)

OTHER PUBLICATIONS

Greenblatt, Ellen, "Have You Ever Wondered . . . ," Datamation, p. 126, Oct. 1997.

(Continued)

*Primary Examiner* — Susanna M Meinecke Diaz
(74) *Attorney, Agent, or Firm* — Greenberg Traurig, LLP

(57) ABSTRACT

This invention provides for a method of (or apparatus for) facilitating the delivery of advice to consumers using a server unit which can store and display the names and characteristics of experts and then rapidly assist in connecting the expert and consumer for real-time communication. The server can also have the ability to receive keywords from the consumer, match those keywords to one or more experts, and tell the consumer how to contact an expert.

20 Claims, 2 Drawing Sheets

Diverse Advice Sources

Information Flow:

Compensation for Advice:

Related U.S. Application Data

Mar. 26, 2002, now Pat. No. 6,801,899, which is a continuation of application No. 09/488,130, filed on Jan. 20, 2000, now Pat. No. 6,223,165.

(60) Provisional application No. 60/125,557, filed on Mar. 22, 1999.

(56) References Cited

U.S. PATENT DOCUMENTS

| | | | |
|---|---|---|---|
| 5,602,905 A | | 2/1997 | Mettke |
| 5,619,991 A | | 4/1997 | Sloane |
| 5,634,012 A | | 5/1997 | Stefik et al. |
| 5,638,432 A | | 6/1997 | Wille et al. |
| 5,694,549 A | | 12/1997 | Carlin et al. |
| 5,696,965 A | | 12/1997 | Dedrick |
| 5,710,887 A | | 1/1998 | Chelliah et al. |
| 5,710,970 A | | 1/1998 | Walters et al. |
| 5,718,247 A | | 2/1998 | Frankel |
| 5,721,763 A | | 2/1998 | Joseph et al. |
| 5,722,418 A | | 3/1998 | Bro |
| 5,724,424 A | | 3/1998 | Gifford |
| 5,751,956 A | | 5/1998 | Kirsch |
| 5,774,534 A | | 6/1998 | Mayer |
| 5,778,367 A | | 7/1998 | Wesinger, Jr. et al. |
| 5,793,851 A | | 8/1998 | Albertson |
| 5,794,221 A | | 8/1998 | Egendorf |
| 5,809,119 A | | 9/1998 | Tonomura et al. |
| 5,818,836 A | * | 10/1998 | DuVal ............................ 370/389 |
| 5,819,092 A | | 10/1998 | Ferguson et al. |
| 5,819,267 A | | 10/1998 | Uyama |
| 5,819,271 A | | 10/1998 | Mahoney et al. |
| 5,825,869 A | | 10/1998 | Brooks et al. |
| 5,825,876 A | | 10/1998 | Peterson, Jr. |
| 5,850,433 A | | 12/1998 | Rondeau |
| 5,862,223 A | * | 1/1999 | Walker et al. .................... 705/50 |
| 5,864,871 A | | 1/1999 | Kitain et al. |
| RE36,111 E | | 2/1999 | Neville |
| 5,870,546 A | | 2/1999 | Kirsch |
| 5,870,744 A | | 2/1999 | Sprague |
| 5,884,032 A | | 3/1999 | Bateman et al. |
| 5,884,272 A | * | 3/1999 | Walker et al. ................. 705/319 |
| 5,884,282 A | | 3/1999 | Robinson |
| 5,893,077 A | | 4/1999 | Griffin |
| 5,907,677 A | | 5/1999 | Glenn et al. |
| 5,911,132 A | | 6/1999 | Sloane |
| 5,914,951 A | | 6/1999 | Bentley et al. |
| 5,937,390 A | | 8/1999 | Hyodo |
| 5,940,471 A | | 8/1999 | Homayoun |
| 5,960,069 A | * | 9/1999 | Felger ...................... 379/114.01 |
| 5,963,202 A | | 10/1999 | Polish |
| 5,963,861 A | | 10/1999 | Hanson |
| 5,978,567 A | | 11/1999 | Rebane et al. |
| 5,982,863 A | | 11/1999 | Smiley et al. |
| 5,991,394 A | | 11/1999 | Dezonno et al. |
| 5,995,705 A | | 11/1999 | Lang |
| 5,999,965 A | | 12/1999 | Kelly |
| 6,026,148 A | | 2/2000 | Dworkin et al. |
| 6,029,141 A | | 2/2000 | Bezos et al. |
| 6,046,762 A | | 4/2000 | Sonesh et al. |
| 6,049,779 A | * | 4/2000 | Berkson ...................... 705/14.39 |
| 6,064,978 A | | 5/2000 | Gardner et al. |
| 6,108,704 A | | 8/2000 | Hutton et al. |
| 6,189,030 B1 | | 2/2001 | Kirsch et al. |
| 6,208,713 B1 | | 3/2001 | Rahrer et al. |
| 6,216,111 B1 | | 4/2001 | Walker et al. |
| 6,223,165 B1 | | 4/2001 | Lauffer |
| 6,230,287 B1 | * | 5/2001 | Pinard et al. ...................... 714/31 |
| 6,243,684 B1 | | 6/2001 | Stuart et al. |
| 6,269,361 B1 | | 7/2001 | Davis et al. |
| 6,275,490 B1 | | 8/2001 | Mattaway et al. |
| 6,327,572 B1 | | 12/2001 | Morton et al. |
| 6,445,694 B1 | * | 9/2002 | Swartz ............................ 370/352 |
| 6,466,966 B1 | | 10/2002 | Kirsch et al. |
| 6,470,079 B1 | | 10/2002 | Benson |
| 6,470,181 B1 | | 10/2002 | Maxwell |
| 6,510,417 B1 | | 1/2003 | Woods et al. |
| 6,516,057 B2 | | 2/2003 | Meek et al. |
| 6,523,101 B1 | | 2/2003 | Lauffer |
| 6,529,878 B2 | | 3/2003 | De Rafael et al. |
| 6,546,372 B2 | | 4/2003 | Lauffer |
| 6,549,889 B2 | | 4/2003 | Lauffer |
| 6,560,576 B1 | | 5/2003 | Cohen et al. |
| 6,731,736 B2 | | 5/2004 | Meek et al. |
| 6,760,537 B2 | | 7/2004 | Mankovitz |
| 6,769,020 B2 | | 7/2004 | Miyazaki et al. |
| 6,801,899 B2 | | 10/2004 | Lauffer |
| 6,826,194 B1 | * | 11/2004 | Vered et al. .................... 370/449 |
| 6,850,965 B2 | | 2/2005 | Allen |
| 6,856,809 B2 | | 2/2005 | Fostick |
| 6,859,833 B2 | | 2/2005 | Kirsch et al. |
| 6,968,174 B1 | | 11/2005 | Trandal et al. |
| 7,076,037 B1 | | 7/2006 | Gonen et al. |
| 7,092,901 B2 | | 8/2006 | Davis et al. |
| 7,103,010 B2 | | 9/2006 | Melideo |
| 7,181,415 B2 | | 2/2007 | Blaser et al. |
| 7,187,761 B2 | | 3/2007 | Bookstaff |
| 7,200,413 B2 | | 4/2007 | Montemer |
| 7,212,615 B2 | | 5/2007 | Wolmuth |
| 7,227,936 B2 | | 6/2007 | Bookstaff |
| 7,231,405 B2 | | 6/2007 | Xia |
| 7,240,110 B2 | | 7/2007 | Haitsuka et al. |
| 7,240,290 B2 | | 7/2007 | Melideo |
| 7,249,045 B2 | | 7/2007 | Lauffer |
| 7,363,254 B2 | | 4/2008 | Skinner |
| 7,434,175 B2 | | 10/2008 | Melideo |
| 7,630,919 B1 | * | 12/2009 | Obrecht ....................... 705/26.4 |
| 2001/0048737 A1 | | 12/2001 | Goldberg et al. |
| 2002/0003867 A1 | | 1/2002 | Rothschild et al. |
| 2002/0010608 A1 | | 1/2002 | Faber et al. |
| 2002/0010616 A1 | | 1/2002 | Itzhaki |
| 2002/0026457 A1 | | 2/2002 | Jensen |
| 2002/0057776 A1 | | 5/2002 | Dyer |
| 2002/0095331 A1 | | 7/2002 | Osman et al. |
| 2002/0107697 A1 | | 8/2002 | Jensen |
| 2002/0122547 A1 | | 9/2002 | Hinchey et al. |
| 2002/0193094 A1 | | 12/2002 | Lawless et al. |
| 2003/0026397 A1 | | 2/2003 | McCroskey |
| 2003/0046161 A1 | | 3/2003 | Kamangar et al. |
| 2003/0083042 A1 | | 5/2003 | Abuhamdeh |
| 2003/0105824 A1 | | 6/2003 | Brechner et al. |
| 2003/0195787 A1 | | 10/2003 | Brunk et al. |
| 2003/0212600 A1 | | 11/2003 | Hood et al. |
| 2003/0220866 A1 | | 11/2003 | Pisaris-Henderson |
| 2003/0223565 A1 | | 12/2003 | Montemer |
| 2003/0225682 A1 | | 12/2003 | Montemer |
| 2003/0231754 A1 | | 12/2003 | Stein et al. |
| 2004/0003041 A1 | | 1/2004 | Moore et al. |
| 2004/0006511 A1 | | 1/2004 | Montemer |
| 2004/0010518 A1 | | 1/2004 | Montemer |
| 2004/0076403 A1 | | 4/2004 | Mankovitz |
| 2004/0174965 A1 | | 9/2004 | Brahm et al. |
| 2004/0174974 A1 | | 9/2004 | Meek et al. |
| 2004/0193488 A1 | | 9/2004 | Khoo et al. |
| 2004/0234049 A1 | | 11/2004 | Melideo |
| 2004/0235524 A1 | | 11/2004 | Abuhamdeh |
| 2004/0247092 A1 | | 12/2004 | Timmins et al. |
| 2004/0249649 A1 | | 12/2004 | Stratton et al. |
| 2004/0254859 A1 | | 12/2004 | Aslanian |
| 2004/0260413 A1 | | 12/2004 | Melideo |
| 2005/0018829 A1 | | 1/2005 | Baker |
| 2005/0041647 A1 | | 2/2005 | Stinnie |
| 2005/0074100 A1 | | 4/2005 | Lederman |
| 2005/0076100 A1 | | 4/2005 | Armstrong |
| 2005/0080878 A1 | | 4/2005 | Cunningham et al. |
| 2005/0096980 A1 | | 5/2005 | Koningstein |
| 2005/0100153 A1 | | 5/2005 | Pines et al. |
| 2005/0105881 A1 | | 5/2005 | Mankovitz |
| 2005/0125416 A1 | | 6/2005 | Kirsch et al. |
| 2005/0135387 A1 | | 6/2005 | Rychener et al. |
| 2005/0209874 A1 | | 9/2005 | Rossini |
| 2005/0240432 A1 | | 10/2005 | Jensen |
| 2005/0245241 A1 | | 11/2005 | Durand et al. |
| 2005/0261964 A1 | | 11/2005 | Fang |
| 2005/0286688 A1 | | 12/2005 | Scherer |

| | | |
|---|---|---|
| 2005/0289015 A1 | 12/2005 | Hunter et al. |
| 2006/0003735 A1 | 1/2006 | Trandal et al. |
| 2006/0004627 A1 | 1/2006 | Baluja |
| 2006/0069610 A1 | 3/2006 | Rossini |
| 2006/0106711 A1 | 5/2006 | Melideo |
| 2006/0136310 A1 | 6/2006 | Gonen et al. |
| 2006/0159063 A1 | 7/2006 | Kumar |
| 2006/0166655 A1 | 7/2006 | Montemer |
| 2006/0171520 A1 | 8/2006 | Kliger |
| 2006/0173827 A1 | 8/2006 | Kliger |
| 2006/0173915 A1 | 8/2006 | Kliger |
| 2006/0182250 A1 | 8/2006 | Melideo |
| 2006/0247999 A1 | 11/2006 | Gonen et al. |
| 2007/0038507 A1 | 2/2007 | Kumer |
| 2007/0100956 A1 | 5/2007 | Kumer |
| 2007/0129054 A1 | 6/2007 | Andronikov et al. |
| 2007/0269038 A1 | 11/2007 | Gonen et al. |
| 2009/0006174 A1 | 1/2009 | Lauffer |

FOREIGN PATENT DOCUMENTS

| | | |
|---|---|---|
| JP | 09233441 | 9/1997 |
| JP | 09319812 | 12/1997 |
| WO | 9804061 | 1/1998 |
| WO | 9847295 | 10/1998 |
| WO | 0057326 | 9/2000 |
| WO | 0127825 | 4/2001 |
| WO | 0128141 | 4/2001 |

OTHER PUBLICATIONS

Kanellos, Michael, "WebWatch: Do You Want to Know the Meaning of Life?," Computer Reseller News, pp. 72-74, Mar. 3, 1997.

"Applying Technology News," Accounting Technology, p. 14, Feb./Mar. 1997.

Allexperts.com, company information retrieved from http://www.allexperts.com, available at least by Apr. 9, 2000.

Answers.com, company information retrieved from http://www.answers.com, available at least by Aug. 8, 2000.

EXP.com, Inc., company information retrieved from http://www.exp.com, available at least by Sep. 20, 2000.

Experts Exchange, Inc., company information retrieved from http://www.experts-exchange.com, available at least by Apr. 9, 2000.

University of Texas—Austin, information on the Electronic Emissary Project retrieved at www.tapr.org/emissary, available at least by Apr. 9, 2000.

Wasik, Joann M., "Information for Sale: Commercial Digital Reference and AskA Services," Virtual Reference Desk, http://www.vrd.org/AskA/commAskA.html, Sep. 20, 1999.

Angelo, Simon, "SurfBrains.com: Brains Online Save Time & Money," M2 Presswire, Jul. 11, 2000.

Ek, Brian, "Walker Digital Issued Landmark U.S. Patent No. 5,862,223 for Global Internet Marketplace for Experts", Business Wire, Jan. 26, 1999.

Hodgson, Cynthia, "Online Expert Databases & Services," Econtent, pp. 48-53, Dec. 1999.

Information Markets Corp., company information retrieved from http://www.infomarkets.com, available at least by Aug. 8, 2000.

Intellectexchange.com, Inc., company information retrieved from http://www.intellectexchange.com, available at least by Aug. 8, 2000.

Kabeya, Kiyoshi et al., "A New Teleconsultation Terminal System Using ISDN," NTT Review, vol. 3, No. 4, pp. 37-43, Jul. 1991.

Ott, Chris, "Making Good on the Information Economy," Denver Business Journal, vol. 51, No. 17, p. 27A, Dec. 17, 1999.

Qcircuit.com, company information retrieved from http://www.qcircuit.com, available at least by Aug. 8, 2000.

Rogers, Michael et al, "Experts Abound at New Web Sites," Library Journal, pp. 22-24, Mar. 1, 2000.

Dalton, Gregory, "Rent-An-Expert on the Web," Information Week, p. 75, Sep. 6, 1999.

Expertcity.com, "About Us," company information retrieved from http://www.expertcity.com, available at least by Apr. 9, 2000.

Wieland, Heidi et al., "Expertcity.com Launches Premier Online Marketplace for Expert Services," PR Newswire, Aug. 30, 1999.

"TriNet's 'Help Me, I'm Stuck' Internet Voice Button Services Pushes Web Pages to Online Users," Business Wire, Mar. 25, 1998.

"Connecting to On-Line Car Shoppers: Auto Sellers Use Netcall Internet Call-Button Technology to Turn 'Clicks' into Interactive Sales," Business Wire, p. 4089, Jul. 19, 1999.

"NetCall Internet Call Buttons Enhance E-Commerce Customer Service and Sales," PR Newswire, p. 7431, Aug. 9, 1999.

Broad, Doug et al., "Lucent Technology and Netscape Team to Deliver Lucent Ecommerce Solutions," Business Wire, Sep. 23, 1998.

Collett, Stacey et al., "Why Online Browsers Don't Become Buyers," Computerworld, vol. 33, No. 48, p. 14, Nov. 29, 1999.

Davey, Tom, "Wheeling and Dealing Online," PC Week, vol. 13, No. 45, pp. 1, 129, Nov. 11, 1996.

Healey, John, "From A-Z: You Can Sell Advice Online," San Jose Mercury News, retrieved from http://www.mercurycenter.com on Oct. 24, 2001.

Keen.com, company information retrieved from http://www.keen.com, available at least by 1999.

Menn, Joseph, "An Expert? There's Now a Home for You on the Internet," Los Angeles Times, retrieved from http://www.denverpost.com on Oct. 24, 2001.

Moore, Michael et al., "USA Global Link Brings Interactively to Internet Shopping," Business Wire, Oct. 7, 1998.

Pelline, Jeff, "Net Firm to Connect Users by Phone," CNET News.com, Nov. 8, 1999.

Tehran!, Rich, "e-Rip Van Winkle and the 60-second Nap," Call Center Solutions, vol. 18, No. 2, pp. 16-18, Aug. 1999.

Keen.com, "Keen.com Launches First Live Answer Community, Connects People with Information to Share Over Their Standard Telephone," company press release, Nov. 8, 1999.

International Application No. PCT/US00/06849, International Search Report, May 16, 2000.

Addeo, E.J. et al., "An Experimental Multi-Media Bridging System," Frontiers in Computer Communications Technology, Computer Communications Review, vol. 17, No. 5, pp. 236-242, Aug. 11-13, 1987.

Asthana, Abhaya et al., "A Small Domain Communications System for Personalized Shopping Assistance," IEEE International Conference on Personal Wireless Communications, Publication No. 0-7803-1996-6/94, pp. 199-203, Aug. 18, 1994.

Becker, Ralph, "ISDN Tutorial: Definitions," retrieved from http://www.ralphb.net/ISDN/defs.html, available at least by Apr. 21, 2000.

Hase, Masahiko et al., "Advanced Videophone System Using Synchronized Video Filing Equipment," NTT Review, vol. 3, No. 4, pp. 29-36, Jul. 1991.

Littleton, Linda, "HDD: A Helpdesk Database," Proceedings of the ACM SIGUCCS User Services Conference XXII, pp. 205-210, Oct. 16-19, 1994.

Ludwig, L.F. et al., "Laboratory for Emulation and Study of Integrated and Coordinated Media Communication, " Conference on Office Information Systems, pp. 283-291, Mar. 23-25, 1988.

Mercalli, Franco et al., "The ESSAI Teleshopping System: An Example of a Broadband Multimedia Application," IEEE Global Telecommunications Conference, pp. 572-576, Nov. 28, 1994.

"Keen.com raises $60 Million from Prestigious Investors and Strategic Partners Just 60 Days After Launch of Its Live Answer Community," Business Wire, Jan. 11, 2000.

International Application No. PCT/US00/10730, International Search Report, Jan. 3, 2001.

Greenberg, Ken, "Jambo Launches to Connect People and Businesses from the Internet to the Phone," Market Wire, May 3, 2005.

Greenberg, Ken, "Jambo Names Netzero Co-founder Stacy Haitsuka to New Post of Chief Information Officer," Business Wire, Jul. 5, 2005.

Greenberg, Ken, "Jambo Receives $5 Million in Financing from Kline Hawkes & Co., Westlake Venture Partners, Others," Business Wire, Oct. 17, 2005.

Jambo, "Welcome to Jambo—The Leader in Pay-Per-Call Solutions," company information retrieved from http://www.jambo.com, available at least by Oct. 17, 2005.

Jingle Networks, Inc:, "Introducing 1-800 FREE411: First Nationwide Free Telephone Directory Assistance Service," Sep. 20, 2005.

ADS-CLICK, "ADS-click Adds Skype-Based Pay-Per-Call Advertising Capabilities to Its Private-Labeled Solution, which will be Unveiled at ad:tech New York," Market Wire, Oct. 10, 2005.

Jingle Networks, Inc., "1-800-FREE411 Provides Two Great Opportunities to Acquire New Customers," available at least by Oct. 20, 2005.

"AtOnce Talks Up E-mail Marketing Campaigns with ITXC Push to Talk Service," Business Wire, Feb. 26, 2001.

"ITXC Corp and Doubleclick Energize Banner Ads with Web Telephony; Companies Voice-Enable Banner Advertisements Using ITXC Push to Talk Service," Business Wire, Dec. 12, 2000.

Ingenio, Inc., "FindWhat.com Enters Agreement with Ingenio to Offer Pay Per Call Advertising Platform," press release available at http://www.ingenio.com, Apr. 7, 2004.

USPTO Transaction History for related U.S. Appl. No. 08/702,833, filed Aug. 23, 1996, entitled "Method for Establishing Anonymous Communication Links," now U.S. Patent Serial No. 5,907,677.

USPTO Transaction History for related U.S. Appl. No. 09/414,710, filed Oct. 8, 1999, entitled "System for Providing Services in Real-Time Over the Internet."

USPTO Transaction History for related U.S. Appl. No. 09/488,130, filed Jan. 20, 2000, entitled "Method and Apparatus to Connect Consumer to Expert," now U.S. Patent Serial No. 6,223,165.

USPTO Transaction History for related U.S. Appl. No. 09/733,872, filed Dec. 8, 2000, entitled "Assistance Method and Apparatus," now U.S. Patent Serial No. 6,523,010.

USPTO Transaction History for related U.S. Appl. No. 09/782,925, filed Feb. 13, 2001, entitled "Assistance Method and Apparatus," now U.S. Patent Serial No. 6,549,889.

USPTO Transaction History for related U.S. Appl. No. 09/782,984, filed Feb. 13, 2001, entitled "Assistance Method and Apparatus," now U.S. Patent Serial No. 6,546,372.

USPTO Transaction History for related U.S. Appl. No. 10/107,743, filed Mar. 26, 2002, entitled "Assistance Method and Apparatus," now U.S. Patent Serial No. 6,801,899.

USPTO Transaction History for related U.S. Appl. No. 10/951,502, filed Sep. 27, 2004, entitled "Method and System to Connect Consumers to Information," now U.S. Patent No. 7,249,045.

USPTO Transaction History for related U.S. Appl. No. 11/772,525, filed Jul. 2, 2007, entitled "Method and System to Connect Consumers to Information."

* cited by examiner

Fig. 1a

Diverse Advice Sources

Compensation for Advice:

Information Flow:

Fig. 1b

METHOD AND SYSTEM TO CONNECT CONSUMERS TO INFORMATION

CROSS REFERENCE TO RELATED APPLICATIONS

The present application is a continuation application of U.S. patent application Ser. No. 11/772,525, filed Jul. 2, 2007, now U.S. Pat. No.7,729,938 which is a continuation application of U.S. patent application Ser. No. 10/951,502, filed Sep. 27, 2004 and now U.S. Pat. No. 7,249,045, which is a continuation application of U.S. patent application Ser. No. 10/107,743, filed Mar. 26, 2002 and now U.S. Pat. No. 6,801,899, which is a continuation of U.S. patent application Ser. No. 09/488,130, filed Jan. 20, 2000 and now U.S. Pat.No. 6,223,165, which claims the benefit of Provisional U.S. Patent Application Ser. No. 60/125,557, filed Mar. 22, 1999, the disclosures of which are incorporated herein by reference.

FIELD OF THE INVENTION

The present invention relates to techniques for delivering information electronically, more particularly, for delivering advice to consumers from a diverse set of experts. Still more particularly, the present invention relates to systems and methods for matching consumers questions with experts, displaying available experts for consumer viewing and selection, providing for compensation from consumers to experts, and providing for the connection between consumer and experts.

DEFINITIONS

Advice: Any needs of the consumer which can be provided for by an expert, including but not limited to conversation, entertainment, sounds or pictures of any kind, text, video, audio. This advice is not limited to that provided by agents regarding company products; it can include medical, legal, educational, travel, entertainment, religious, and other forms of advice. In addition, herein "advice" is meant broadly to include any type of information, comfort, or communication a consumer desires.

Consumers: Individuals, companies, organizations, governments, or devices which have one or more questions or needs for advice.

Experts: Individuals, companies, organizations, governments, or devices which are able to provide advice to consumers, provided that experts' initial means to contact consumers is via the server in the Advice Router. Experts' compensation, which may be zero, can come from either consumers directly or from the Advice Router. Collectively, experts represent a broader range of knowledge and experience than do agents which work for a single company. Much as the word "advice" is used broadly, "expert" is meant broadly-since-many types of information can be given by human beings.

Agents: Individuals, companies, organizations, governments, or devices who, as part of their relationship/employment at that institution, answers questions when connected to his institution's telephone or server, provided that the agent is paid by the institution for that function. The advice provided for by agents is generally restricted to that regarding products offered by their respective company.

Server: any device, network or software which connects consumers and experts.

Query: an action initiated by a consumer which includes keywords or other means to summarize their question or need for advice.

Expert characteristics: used for matching with consumers queries. Including, but not limited to one or more of the following: a code name which does not include his real name; keywords of expertise; number of years experience in each area of expertise; degrees earned; number of years of school after completion of high school or college; companies worked for or schools/training programs attended in the past or present; age; language; neighborhood, city, state, and/or country of residence; quality score as judged by previous consumer interactions; compensation rate for consumer advice; and whether the expert is available at the actual moment of consumers query or within 1, 2, 5, 10, 15, 30, 60 minutes.

Matching: a process for scoring and putting in an order of relevance a list or selected list of experts who are likely to be able to answer a consumer's query. Can involve any method of assignment of numbers to the number of keyword matches or matches between ranges of characteristics desired by the consumer with the actual expert characteristics.

Logged in, or on-line: detectable means of communication between server and expert, including but not limited to telephone, Internet telephony, email, audio, and/or video.

Means to contact: any method, information, or technology used to bring together the consumer with one or more experts, including but not limited to telephone, Internet telephony, email, audio, and/or video. Means to contact includes telephone numbers (including toll-free and pay-per-call numbers), email addresses, Internet web pages or sites, video-conferencing details. More preferably, the means of contact includes telephone, Internet telephony, audio, and/or video, and even more preferably Internet telephony, audio and/or video, and even more preferably video. The technology to be used for any of the above includes TVs, TVs with set-top web browsers, PCs, telephones, and satellite connections.

Time-to-connect: the period of time between the transmission of the means of contact and the actual connection between expert and consumer. In the case where the consumer selects an expert, the time-to-connect is the period of time beginning when at the consumer's last action (e.g., clicking on the symbol for an expert or his telephone number) and ending when the actual connection is made. In the case where the server makes both connections, the time-to-connect is the period of time beginning when the server indicates to the consumer that it is beginning to contact the expert and ending when the actual connection is made.

BRIEF DESCRIPTION OF THE FIGURES

FIG. 1.a shows the most common arrangement today of the advice business, known as Centralized Advice Sources, where there are a large number of consumers and few agents to help them at each company; this has the general shape of a funnel with too many questions going to too few agents.

FIG. 1.b shows a fundamentally new advice technology structure, Diverse Advice Sources, wherein the actual companies selling products are not involved or only peripherally involved. Diverse Advice Sources more evenly equalizes the number of questions in the world at a given point in time with the number of experts who are likely to be able to answer their questions. This technology is in an hourglass shape where a large number of experts is available rather than the small number of agents at each company. In the middle is a new form of information company, the Advice Router, which rapidly facilitates the matching of and connection between consumers and experts.

BACKGROUND

Problems with Customer Service and General Advice

As more technology (videorecorders, personal computers, Internet, TV web boxes, cell phones, etc.) enters peoples' lives, there is greater and greater demand for help in choosing devices and solutions and in setting them up and correcting problems. Even more generally, there is greater need for assistance in daily life, whether it is for medical, legal, family, or entertainment reasons.

At the same time that more information is required to conduct our lives, available effective sources of that information have not grown sufficiency in number or efficiency.

Companies selling products often have web pages or telephone support lines, but these are either too restricted in information, or the consumer must wait for long periods for live help.

To help with the routing of calls to available agents in a company, Cave (WO9813765) has devised a real-time system wherein a queuing manager routes calls to an agent who is free at the time. The system still involves automated answering systems which many consumers find frustrating, and it requires the hiring of not only agents but the queuing manager.

In the future, streaming audio and video capabilities on the web will make it possible for company agents to speak directly to consumers. However, this will be very costly to operate and the consumer will probably have to wait for long times to speak to one of the agents.

For general advice, the Internet is far too inefficient for many uses. Search engines return many hits, requiring the consumer to try many web sites and hope that the answer is available.

1-900 phone numbers (pay-per-call) are limited in scope and consumers hesitate to use them due to high per-minute rates, lack of trust in the billing, and generally perceived notions that the 900 numbers are for less-than-serious concerns such as astrology or sex chat. In addition, 900 services are small and narrowly focused, without the benefits of the Diverse Advice Sources arrangement, and they did not include matching and/or display technologies.

Figure 1A:
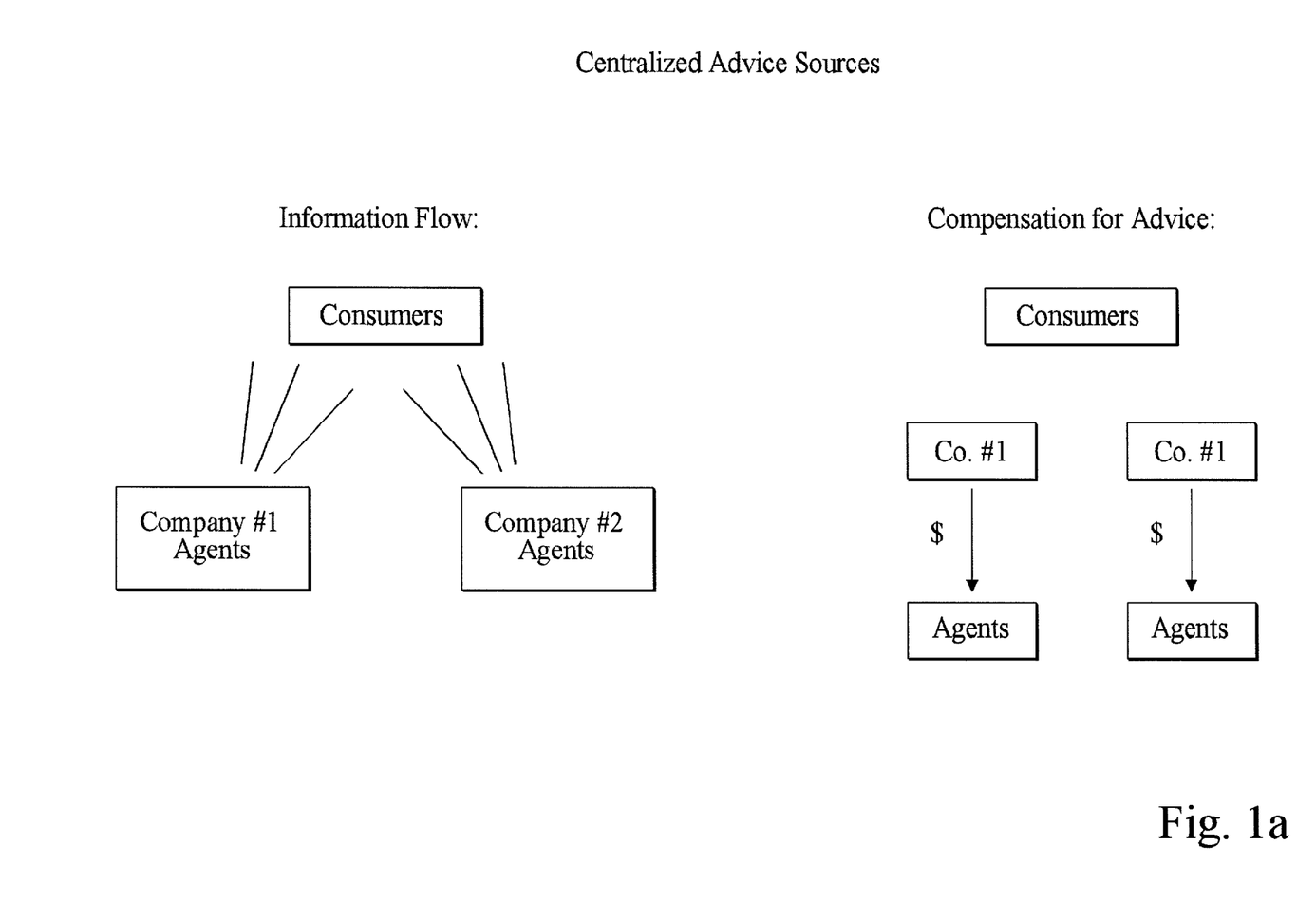

As shown in FIG. 1.a, the fundamental problem with current advice technologies is that there are a large number of consumers and few agents to help them at each company; this is known as Centralized Advice Sources, and the has the general shape of a funnel with too many questions going to too few agents. This leads to high cost (to pay agents and purchase systems), slow response time (long hold times on telephone), and lack of personal service (live agents). In addition, the agents often can only answer a limited range of questions regarding the companies products. Thus, the participation and control of the consumer advice function by each company is fundamentally hurting the company by frustrating consumers and by requiring it to staff, manage, and pay for a vast and complex undertaking which is, outside of its main expertise (making widgets, providing a narrow service, etc.).

Previous solutions have not adequately filled the need, particularly for immediate advice or connection between appropriate people.

The American Information Exchange (AMIX) was a central exchange that attempted to mediate between buyers and sellers of information. But the complexity and lack of immediacy, among other problems, limited its ability to efficiently solve the buyer's problem.

Walker (U.S. Pat. No. 5,862,223) envisioned a similarly complex exchange, often involving several lengthy steps where a user request is submitted; a search of experts, even beyond its members, is undertaken; a portion of the user request (question) is transmitted to the computer-selected expert, etc. until the request if fulfilled. Walker (col 8, line 49; col 24, line 67) allows the user himself to select the expert from a general list, but there is no provision for seeing which expert is available at that instant to talk, and there is no provision to make the process of connecting the expert and user quickly, say within 1 min or 10 seconds. In addition the user must submit a portion of his question (end user request).

In the complex process described by Walker, the expert and user can communicate in real-time (col 9, line 1; col 26, line 49), but only after the process of submitting the end user request to the expert.

In another embodiment of Walker (col 28, line 66), the end user calls the central controller and eventually is put in touch with an expert for a real-time connection. No allowance is made for the central controller to make two separate calls (thus connecting the expert and user) after the user selects the expert.

In addition, there are no constraints in Walker on how fast the time-to-connect process needs to be to be useful. Timely information is more highly valued than delayed information.

Moreover, the detailed lists of experts and their characteristics (resumes, etc.) that are displayed in Walker (col 25, line 35) are not suitable for a system that fills the need for rapid selection and connection between parties; as the number of experts grows, there will be simply too many pages of text to scroll through. There is needed a new display system where users can rapidly survey the available experts via information-rich graphics.

Walker does not take into account the use of experts as a workforce for customer support. No mention is made of product or service companies issuing certification for experts, and, in turn, those certifications listed or displayed explicitly by the central controller/server.

DESCRIPTION

Figure 1B:
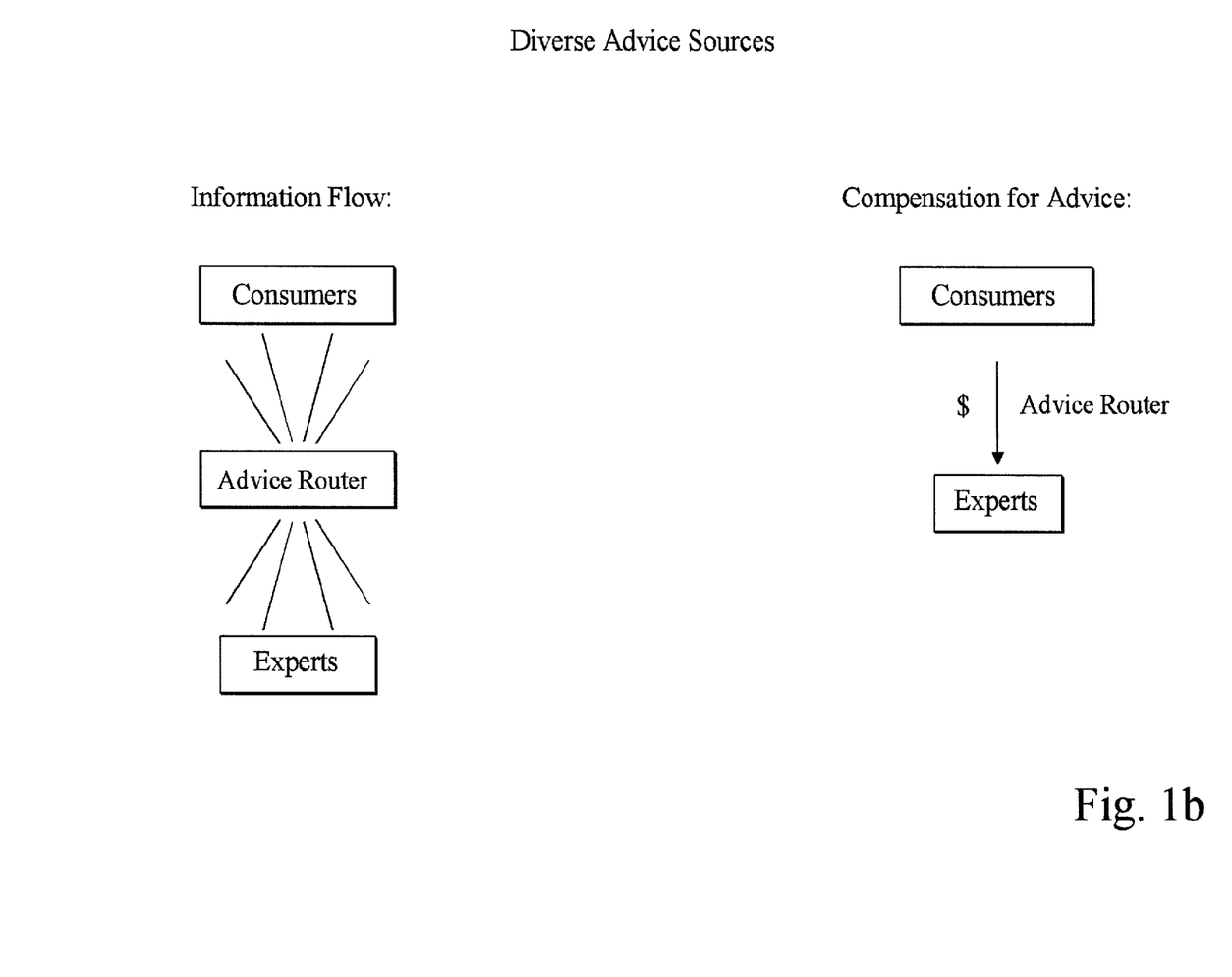

In one embodiment, this invention provides for a fundamentally new advice technology structure, Diverse Advice Sources, wherein the actual companies selling products are not involved or only peripherally involved. Diverse Advice Sources more evenly equalizes the number of questions in the world at a given point in time with the number of experts who are likely to be able to answer their questions. As shown in FIG. 1.b this technology is in an hourglass shape where a large number of experts is available rather than the small number of agents at each company. In the middle is a new form of information company, the Advice Router, which rapidly facilitates the matching of and connection between consumers and experts.

The sheer number of experts available in Diverse Advice Sources solves the arithmatic (funnel) problem of Centralized Advice Sources, leading to the two most important benefits: fast response and the routine availability of live experts. In addition the diversity of sources raises the likelihood that the consumer will get more holistic advice, not limited to the tools available from any one company.

In another embodiment, this invention provides for a method of (or apparatus for) facilitating the delivery of advice to consumers, comprising:

providing a server unit with the ability to store the names or identification of two or more experts, said experts coded by one or more expert characteristics, said server having the ability to detect which experts are online;

said server having the ability to display at least one of said expert characteristics with information-rich graphics or symbols;

said server having the ability to respond to a consumer's selection of expert by either sending the consumer a means to contact expert or by connecting the consumer and expert for real-time communication;

wherein the time-to-connect between consumer and expert is 30 minutes or less.

In another embodiment, this invention provides for a method of (or apparatus for) facilitating the delivery of advice to consumers, comprising:

providing a server unit with the ability to store the names or identification of two or more experts, said experts coded by one or more expert characteristics, said server having the ability to detect which experts are online;

said server unit having the ability to receive one or more keywords from a consumer;

said server unit having the ability to match those keywords to one or more experts and send the consumer a means to contact;

wherein the time-to-connect between consumer and expert is 30 minutes or less.

Certification

In the transition from central to diverse advice sources, companies will find that it is economical to broaden its customer support workforce to non-employees. While these non-employees may not have as detailed or as frequent training, they can answer many of the questions consumers have. Thus a company can offer simple tests and, optionally, transmit the results of those tests to the server, which maintains an up-to-date status of each expert. Alternatively, the company can simply give the certification to the expert who transmits the results to the server.

Certification tests can take many forms, including but not limited to web-based questionnaires, phone, Internet, or face-to-face interviews, live video connections, etc. Optionally, a company can use authentication procedures (fingerprint, voiceprint, "cookies" the expert's computer, passwords, etc.) to ensure the expert's identity. Optionally, the test and results can be cryptographically transmitted between the company and expert; or between the company and server.

Certification can also come from organizations or schools or governments.

Matching

In another embodiment, this invention provides for a matching system or relevance scoring method which finds the best expert to answer a consumer's question. This can involve any method of assignment of numbers to the number of keyword matches or matches between ranges of characteristics desired by the consumer with the actual expert characteristics. This technology is well known for search engines like Yahoo! for finding matches between a consumer's keywords and web pages as well as eBay for finding matches for merchandise.

However, a system and method does not currently exist that allows one to match a wide array of features, including, but not limited to, two or more of the following expert characteristics: a code name which does not include his real name; keywords of expertise; number of years experience in each area of expertise; degrees earned; number of years of school after completion of high school or college; companies worked for or schools/training programs attended in the past or present; age; language; neighborhood, city, state, and/or country of residence; quality score as judged by previous consumer interactions; compensation rate for consumer advice; and whether the expert is available at the actual moment of consumers query or within 1, 2, 5, 10, 15, 30, 60 minutes.

It is preferred that the number of categories in the list of expert characteristics used for matching be at least four, such as code name, keywords, compensation rate, and time availability. More preferably, the number of categories should be at least six. Even more preferably, the number of categories should be at least eight. Most preferred, the number of categories should be at least ten.

In another embodiment, this invention provides for a system for and method of displaying selected experts to the consumer. This includes, at a minimum, conveying, through means that include but are not limited to telephone, Internet telephony, email, audio, and/or video, a way for the consumer to contact the expert (the means of contact). It is more preferred for that conveyance to be performed by Internet telephony, email, audio, and/or video. It is most preferred for that conveyance to be performed by audio, and/or video.

The number of experts presented to the consumer can be at least one. It is more preferred that the number of experts presented to the consumer is at least two. It is even more preferred that the number of experts presented to the consumer is at least five. It is even more preferred that the number of experts presented to the consumer is at least ten. It is even more preferred that the number of experts presented to the consumer is at least 20. It is most preferred that the number of experts presented to the consumer is over 100.

In another embodiment, this invention provides for a system for and method of protecting the privacy and identity of both the expert and the consumer. If the expert prefers, his actual name, address and other information will be withheld from the consumer. Also, individual entries in the expert characteristics list can be shielded from view by the consumer. The consumer likewise can be protected. While privacy has been provided for in commercial/advertising technologies (see Goldhaber, U.S. Pat. No. 5,855,008), the shielding but still utilizing detailed expert characteristic lists has not been provided for.

Display

In addition to the mere conveyance of the means of contact, it is more preferred for the consumer to be presented with a visual display of available experts. Systems and methods have been used by Yahoo! and others for displaying game-playing individuals, with information related to availability for a game now, skill level, and code name. No such system or method exists for displaying expert characteristics.

Display methods include but are not limited to information-rich graphics such as objects with varying color or density, bar graphs, line graphs, 3-D graphs, icons, pictures, photographs, video. All of the above can include animation or motion to attract attention. Words and numbers can be added on or near any of the above to give further expert characteristics. Any of the above can be addressable by mouse/cursor location so that the consumer can easily select which expert to choose or which set of experts to zoom in on and view more closely. Optionally, zoom (magnification) and/or rotation functions can also be used. The zoom function can allow new and more detailed expert characteristics to appear with each increase in magnification. Similarly rotations of objects can reveal more detailed expert characteristics.

Useful expert characteristics that can be displayed visually include, but are not limited to: the expert's quality (rating) score, whether the expert is online now, or how long until he will be; whether the expert has a separate phone line, and whether it is busy or not.

A legend can optionally be provided when abstract symbols or colors are used so that consumers can tell what each symbol or color means.

In another embodiment, experts can select their own symbol, pictures, logos, etc. to advertise themselves (as advertisers). These include all of the above options. Optionally, they can use online avatars to represent themselves, with the additional option of the voice and facial expression of the expert transmitted to the consumer via this avatar.

In another embodiment, a special symbol/notation is displayed next to or as part of an experts symbol if he has been certified by selected companies or organizations. The symbol/notation can optionally expire, disappear, or change its characteristics (color, etc.) after a certain length of time so that the expert is forced to take tests to maintain certification.

In another embodiment, the display is a map either of geography, system or building architecture or any type of display where experts are, at that time, located or qualified in. The map and expert symbols on it is continually updated to see who is online and/or their exact or general location. The size of the symbol used for each expert is adjusted as the number of experts online increases so each can be displayed. Optionally the zoom function allows better viewing of crowded regions of the map.

This display method can be useful in cases where a consumer only wants information from someone at a particular location, e.g., to determine weather, sport conditions (ski, surf, etc), traffic, delivery/pickup truck availability, nature (animal sightings), entertainment (club-hopping), state or city laws, or any kind of location-dependent information.

Other types of non-geographical maps or diagrams can also be used, including but not limited to software architecture, flow charts, graphs, etc. Here the location of the expert's symbol is determined by their expertise in a particular subject within that map.

In some cases, if the expert is qualified in more than one area, two or more of his symbols may appear in a given map or diagram.

Graphical displays (line or scatter plots, etc) can be used by the consumer to weigh different features of the experts before making a selection. The consumer can be given a choice of 2- or 3-dimensional, and what the axis of the graph represent: quality score, compensation rate, distance from the consumer, etc. The symbols for the available experts in a particular subject area are placed in their appropriate position of the graph and the consumer can see, for example a scattergram and pick a well-rated expert who is not too expensive.

It is more preferred that the display method graphically show at least the following two items: relevance score or order of preference of experts on the one hand, and the time availability of the expert on the other. The latter refers to whether the expert is available at the actual moment of consumers query or within 1, 2, 5, 10, 15, 30, 60 minutes. It is even more preferred that the display method graphically show at least the following three items: relevance score or order of preference of expert, the time availability of the expert, and the compensation rate for consumer advice with that expert. It is even more preferred that the display method graphically show at least the following four items: relevance score or order of preference of expert, the time availability of the expert, the compensation rate for consumer advice with that expert and the quality score as judged by previous consumer interactions. It is most preferred that the display method graphically show at least the following five items: relevance score or order of preference of expert, the time availability of the expert, the compensation rate for consumer advice with that expert, the quality score as judged by previous consumer interactions, and one item selected from the following list: number of years experience in each area of expertise; degrees earned; number of years of school after completion of high school or college; companies worked for or schools/training programs attended in the past or present; age; language; neighborhood, city, state, and/or country of residence.

Compensation

Diverse Advice Sources fundamentally changes the economics of the consumer advice business. As shown in FIG. 1, Diverse Advice Sources replaces the awkward arrangement in Centralized Advice Sources wherein individual companies are expected to pay for consumer advice (by paying their hired agents) when it is the consumer who is benefiting from the advice. Of course consumers had in the past expected companies to pay for this advice, to encourage the consumer to use their product and not products from competing companies. The companies respond by establishing limited consumer advice groups which are highly inefficient and costly to the company. In Diverse Advice Sources, the consumer pays for the advice information packet directly, to either or both of the expert and the Advice Router.

This invention also includes an alternative case where the consumer does not directly pay either the expert or the Advice Router. In this special case, general advertisements are used to fund the Advice Router, and the Advice Router either compensates the expert for his time, or the expert receives no direct compensation and instead gains some other value (e.g., advertising).

Unique payment systems and methods used by the Advice Router include but are not limited to the following:

a) credit card or (cyber-money) accounts for one or both of the consumer and expert; proper deductions and credits are made to each account after each transaction.

b) the means of contact can include a 900 number (or similar per-per-call/pay-per-view technology for the Internet); in this case, the consumer simply dials the 900 number given by and controlled or contracted for by the Advice Router, and the expert is paid according to well-known 900 number technology. This 900 number technology has been used in the past to provide advice from individual groups, but these activities did not include matching and/or display technologies, nor did they have the benefits of the Diverse Advice Sources arrangement.

c) other phone or media accounts.

Various payment schemes can be optimized to meet consumer and expert expectations. For example, rather that a flat per-hour, per-minute, or per-session rate, a number of schemes can be used to compensate for the consumer ensuring that the expert is adequate (for example, the first two minutes free), etc.

In all of these cases, the Advice Router can receive a fee for conveying the means of contact, and/or the connection.

Also, the Advice Router can pay or rebate a portion of the consumer charge if the consumer take some additional action, such as rating the quality of the expert, etc.

Connection

This invention provides for a system and method whereby the server used by the Advice Router can be used for providing for or aiding rapid connections and monitoring of interactions between consumers and experts.

Regarding the connection, it is preferred that the server provide for or facilitate a connection within 30 minutes after the means of contact has been conveyed to the consumer. It is more preferred that the time-to-connect is 10 minutes or less. It is even more preferred that the time-to-connect is 5 minutes or less. It is even more preferred that the time-to-connect is 2 minutes or less. It is even more preferred that the time-toconnect is 1 minute or less. It is even more preferred that the time-to-connect is 30 seconds or less. It is even more preferred that the time-to-connect is 20 seconds or less. It is most preferred that the time-to-connect is 10 seconds or less.

The connection can include any method or technology used to bring together the consumer with one or more experts, including but not limited to telephone, Internet telephony, email, audio, and/or video. More preferably, the connection involves telephone, Internet telephony, audio, and/or video, and even more preferably Internet telephony, audio and/or video, and even more preferably video. The technology to be used for any of the above includes TVs, TVs with set-top web browsers, PCs, telephones, and satellite connections.

In the case where the consumer selects an expert on the Internet, the server can connect both using a two-step procedure wherein two separate and independent transmissions (e.g., telephone calls) are placed and then the two transmissions are joined together. This allows the server to store the expert addresses/phone numbers anonymously and control the connection.

The server should be able to monitor the interactions to provide for quality control and/or exact payment.

EXAMPLE

Two experts, Joe and Bill, connect to the Advice Router and fill out forms describing their expertise. Joe is expert in Microsoft's Word and Powerpoint programs, and Bill is expert in the Word and Excel programs. The server detects that they are both logged on. Later that evening, Bill is busy with a consumer for a period he estimates will be 15 more minutes. Joe is free. At that moment, David, a consumer, logs on and fills out a keyword query list that best suits his question: how to turn off the automatic spellchecker in Microsoft Word. He also gives his VISA credit card number via a secure link. A second after he finishes his entry, a display on his PC shows two color-coded boxes coinciding with the current list of available experts, Joe and Bill (only their code names are used, however). The relevance score for both is 1.0 (optimal) since both are experts in Microsoft Word. Both experts also charge the same rate, $1.00 per minute. However, a small box in Joe's area is clearly green and easy to read—this box corresponds to the fact that Joe is available at this instant to speak to David. (David does not select Bill since the red color in his box corresponds to a 15 min. wait or more.) David clicks an icon in Joe's box and a second or two later, a streaming real-time video of Joe appears on David's PC, and if David's PC is so enabled, Joe sees David in his PC. They spend five minutes solving David's problem and log out. Prior to logging out, however, David receives a $0.50 rebate on the cost of the connection by rating the quality of Joe's help, from 0 for "awful" to 10 for "great" The cost of David's call is $5.00 minus $0.50 or $4.50; in his case, this is added to his monthly $50-$100 phone/Internet bill.

For maintaining the site, the Advice Router deducts $1.00 from the net $4.50 received and remits $3.50 to Joe. If David had not elected to receive the $0.50 rebate, the Advice Router would have made $1.50 on the call.

For most of its experts, the Advice Router takes out 30% before paying the experts.

Those skilled in the art will know that this example is illustrative only and does not in any way limit the range of applications of the present invention.

The invention claimed is:

1. A non-transitory machine-readable medium having stored thereon a set of instructions, which when executed on a computing device causes the device to perform a method, the method comprising:
    providing to a user a visual display advertisement on a media channel on behalf of an advisor, wherein the visual display advertisement includes at least a user selectable reference to establish a real-time communication connection with the advisor, an indication of whether the advisor is currently available to communicate via real time communication at a time when the user is viewing the visual display advertisement, and a display of an item associated with the advisor selected from a group consisting of a compensation rate for the advisor and a quality score for the advisor, wherein the visual display advertisement advertises the advisor to the user at least partially based on an order relative to other advisors, the order at least partially based on one or both of the compensation rate and the quality score;
    while the advisor is currently available, receiving a user selection of the user selectable reference corresponding to the advisor, and a central controller using the user selection of the user selectable reference to establish a real-time communication connection between the advisor and the user prior to the user submitting a question for the advisor including the central controller using the user selection to establish a real-time communication connection with the advisor and with the user prior to the user submitting a question for the advisor, wherein the establishing the real-time communication connection comprises the central controller originating a first communication connection to the advisor and a second communication connection to the user; and
    charging an amount for the real-time communication connection established between the advisor and the user based at least in part on the compensation rate.

2. The medium of claim 1, wherein the first communication connection comprises a first telephonic connection, and the second communication connection comprises a second telephonic connection.

3. The medium of claim 1, wherein the media channel includes at least a portion of Internet.

4. The medium of claim 1, wherein the user selectable reference includes a hyper-link to be selected by the user.

5. The medium of claim 1, wherein the method further comprises:
    providing visual display advertisements on a media channel on behalf of multiple advertisers, the visual display advertisements to include at least a reference to a telephonic connection with the respective advertisers; and
    charging an amount each time a telephonic connection is established between a respective advertiser and a customer.

6. The medium of claim 1, wherein the visual display advertisement is provided in response to a search submitted by the user.

7. The medium of claim 6, wherein the visual display advertisement is provided in response to a search submitted by the user for a geographic location.

8. The medium of claim 6, wherein the visual display advertisement is provided in response to a search submitted by the user for a subject matter.

9. The medium of claim 6, wherein the visual display advertisement is provided in response to a keyword search submitted by the user.

10. The medium of claim 1, wherein the method further comprises:
charging an amount for each telephonic connection established between the advisor and the user based on the visual display advertisement.

11. The medium of claim 1, wherein the charging of the amount comprises deducting the amount from an amount received from the user.

12. The medium of claim 1, wherein the charging of the amount comprises charging the user.

13. The medium of claim 1, wherein the amount charged is according to a price specified by the advisor.

14. The medium of claim 1, wherein the real-time communication connection includes a telephonic connection established between the advisor and the user according to the visual display advertisement and the telephonic connection is provided by Internet telephony.

15. The medium of claim 1, wherein the real-time communication connection includes a telephonic connection established between the advisor and the user according to the visual display advertisement and the telephonic connection includes video.

16. An apparatus, comprising:
a server unit to provide a visual display advertisement to a user on a media channel, the visual display advertisement advertising availability of an advisor to provide advice, wherein the visual display advertisement includes at least a user selectable reference to establish a real-time communication connection with the advisor, an indication of whether the advisor is currently available to communicate via real time communication at a time when the user is viewing the visual display advertisement, wherein the visual display advertisement advertises the advisor to the user at least partially based on an order relative to other advisors, the order at least partially based on one or both of a compensation rate and a quality score; and
a central controller coupled with the server unit to receive a user selection of the user selectable reference corresponding to the advisor while the advisor is currently available, and to, prior to the user submitting a question for the advisor, establish a real-time communication connection with the advisor and with the user using the selection from the user prior to the user submitting a question for the advisor, wherein the establishing the real-time communication connection comprises the central controller originating a first communication connection to the advisor and a second communication connection to the user;
wherein an amount is charged for the real-time communication connection established between the advisor and the user, by one or both of the server unit and the central controller, based at least in part on the compensation rate.

17. The apparatus of claim 16, wherein the real-time communication connection includes a telephonic connection established between the advisor and the user according to the visual display advertisement and the telephonic connection is provided by Internet telephony.

18. The apparatus of claim 17, wherein the telephonic connection includes video.

19. A method, comprising:
providing to a user a visual display advertisement on a media channel, the visual display advertisement advertising availability of an advisor to provide advice, wherein the visual display advertisement includes at least a user selectable reference to establish a real-time communication connection with the advisor, an indication of whether the advisor is currently available to communicate via real time communication at a time when the user is viewing the visual display advertisement, wherein the visual display advertisement advertises the advisor to the user at least partially based on an order relative to other advisors, the order at least partially based on one or both of a compensation rate and a quality score;
while the advisor is currently available, receiving a user selection of the user selectable reference corresponding to the advisor, and a central controller using the user selection of the user selectable reference to establish a real-time communication connection between the advisor and the user prior to the user submitting a question for the advisor including the central controller establishing a real-time communication connection with the advisor and with the user prior to the user submitting a question for the advisor, wherein the establishing the real-time communication connection comprises the central controller originating a first communication connection to the advisor and a second communication connection to the user; and
charging an amount for the real-time communication connection established between the advisor and the user based at least in part on the compensation rate.

20. The method of claim 19, wherein the real-time communication connection includes a telephonic connection established between the advisor and the user according to the visual display advertisement and the telephonic connection is provided by Internet telephony.

* * * * *